US007162057B1

(12) United States Patent  
Roth et al.

(10) Patent No.: US 7,162,057 B1  
(45) Date of Patent: Jan. 9, 2007

(54) APPARATUS FOR AND METHOD OF MONITORING PARTICULATE MATERIAL IN A FLUID

(75) Inventors: Nicholas James Roth, Berkshire (GB); John Robert Roth, Berkshire (GB); Roderick Clive Gaskin, Berkshire (GB)

(73) Assignee: Jorin Limited, Sandhurst (GB)

( * ) Notice: Subject to any disclaimer, the term of this patent is extended or adjusted under 35 U.S.C. 154(b) by 0 days.

(21) Appl. No.: 09/890,648

(22) PCT Filed: Mar. 2, 2000

(86) PCT No.: PCT/GB00/00336

§ 371 (c)(1),  
(2), (4) Date: May 9, 2002

(87) PCT Pub. No.: WO00/46586

PCT Pub. Date: Aug. 10, 2000

(30) Foreign Application Priority Data

Feb. 5, 1999 (GB) .................................. 9902549.6

(51) Int. Cl.
*G06K 9/00* (2006.01)
*F17D 1/16* (2006.01)
*F17D 1/18* (2006.01)
*F15C 1/00* (2006.01)
*G01J 1/10* (2006.01)

(52) U.S. Cl. .................. 382/107; 137/13; 137/803; 356/243.2

(58) Field of Classification Search ................ 382/100, 382/107; 137/13, 803; 356/246, 243.2; 250/432 R, 435–436  
See application file for complete search history.

(56) References Cited

U.S. PATENT DOCUMENTS 4,075,462 A * 2/1978 Rowe ........................... 377/10  
4,283,128 A * 8/1981 Meyer et al. ................ 396/432  
6,184,978 B1 * 2/2001 Kasdan et al. .............. 356/246

FOREIGN PATENT DOCUMENTS

EP 0311 368 5/1988  
EP 0 311 368 * 4/1989

\* cited by examiner

*Primary Examiner*—Jingge Wu  
*Assistant Examiner*—Shefali Patel  
(74) *Attorney, Agent, or Firm*—Dickstein Shapiro LLP

(57) ABSTRACT

Apparatus for monitoring particulate material in a fluid comprising a passageway (17), through which fluid to be monitored is passed, at least a portion (24) of the boundary of the passageway (17) being translucent to enable radiation to pass through that portion (24). A camera (40) is arranged to receive such radiation and is constructed to generate electrical signals representative of the images it receives. Image analysis means (57) are connected to receive those electrical signals and to provide data from them relating to the particulate material contained within the fluid.

15 Claims, 5 Drawing Sheets

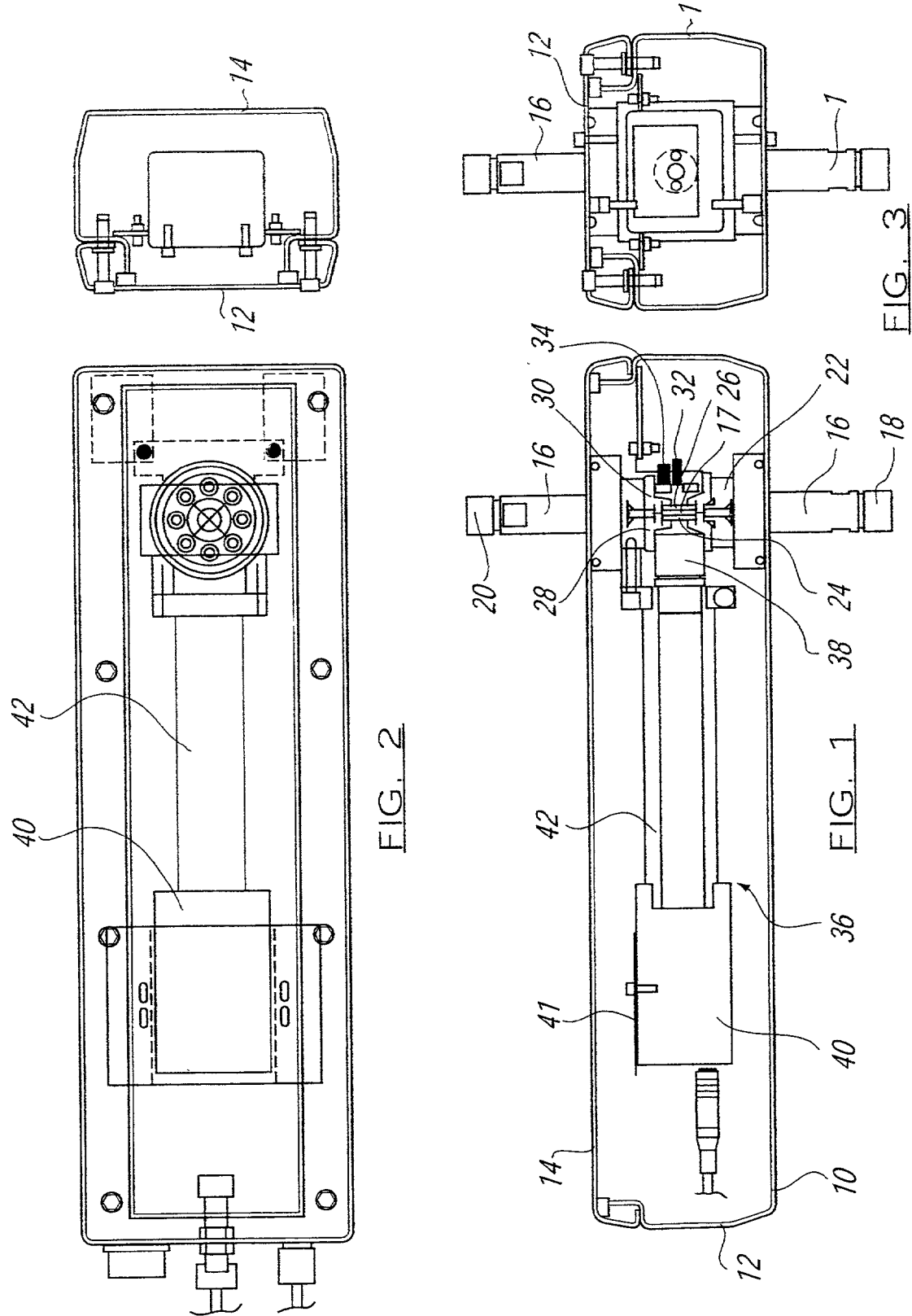

APPARATUS FOR AND METHOD OF MONITORING PARTICULATE MATERIAL IN A FLUID

The present invention relates to apparatus for monitoring particulate material in a fluid, as well as to a method of monitoring particulate material in a fluid, whether the particulate material comprises a liquid, a solid, or a gas.

One method of doing this, which has already been proposed, involves the scattering of light by such particles and observing the relative strength of light scattered as a function of the angle of scattering. Mie theory is then used to calculate particle size distribution according to the data collected.

One shortcoming of this method is that the theory presumes at least on average that the particles are generally spherical so that it cannot distinguish between spherical particles and non-spherical particles.

It is also necessary to provide more than one sensor viewing a specified target area at respective different angles.

The present invention seeks to obviate one or more of the foregoing shortcomings.

Accordingly, the present invention is directed to apparatus for monitoring particulate material in a flowing fluid comprising a passageway, through which fluid to be monitored is passed, at least a portion of the boundary of the passageway being translucent to enable radiation to pass through that portion, a camera, which is arranged to receive such radiation and which is constructed to generate electrical signals having a multiplicity of different values respectively representative of different values of a grey scale, the signals as a whole thereby being representative of the images received by the camera, a frame grabber connected to the camera to isolate a frame from the signals generated by the camera, a background memory connected to the frame grabber to store data indicative of the value of background signals of the image seen by the camera, subtraction means connected to the background memory and to the frame grabber to subtract the stored values of the background signals from those of the signals of a subsequent frame isolated by the frame grabber, and an image analyser connected to receive signals of successive frames from the frame grabber, after such subtraction, so as to provide data on each successive isolated frame relating to the particulate material contained within the flowing fluid.

One benefit of such a construction is that particles which have adhered to the said portion will be disregarded in subsequent image analysis, so that such adhering particles will not skew the results.

Preferably, the said portion is transparent.

The camera may be a stills camera triggered to operate by the image analysis means.

The camera is desirably a Charged Coupled Device (CCD) camera.

The radiation may be in the visible range of the electromagnetic spectrum.

Preferably, the said electrical signals representing a grey scale, range in value from zero to 255, in which a zero value can be for the darkest image for a given period and 255 the brightest, or vice versa.

In the sense that the signals represent different pixels as different respective values of a grey scale, they are in this specification referred to as analogue signals, even though each value may be coded in eight bits of a byte in what would conventionally be referred to as a digital signal. In the present context, a digital signal is one in which each pixel is represented by one of only two values.

Advantageously, out-of-focus means are provided to eliminate images of particles which are out of focus when viewed by the camera. This may be achieved by means which check the rate of change in the value of signals received for successive pixels of the image progressing from a position away from the particle to a position well within the boundary of the particle image, and eliminating that particle image if the rate of change of the values of the signals never exceeds a predetermined threshold value.

To eliminate skewing from half portions of particle images at the very edge of the field of view, any particle image which is closer than a predetermined distance to the edge of the field of view may be eliminated by edge-of-field elimination means.

Preferably, the image analyser is further provided with an analogue-to-digital converter in which any pixel having a value beyond a predetermined threshold value in the analogue input is accorded one of two values in the digital output, and any pixel having a value equal to or below the said threshold value is accorded the other of the two values in the digital output. This provides the advantage that subsequent analysis of the data may be effected simply by counting successive adjacent pixels having the said one value in one or more given directions across the field of view. In addition, for example, the total number of pixels of the said one value for a given particle image may be counted to give the total area of the field of view occupied by the particle, or the total number of pixels around the circumference of the particle image may be counted to provide a value for the perimeter of the particle.

Preferably, the fluid is backlit so that the silhouettes of particles are viewed by the camera.

Preferably, the said portion comprises at least one sapphire window, to reduce the likelihood that the said portion will be scratched and thus rendered less transparent.

The present invention extends to a method of monitoring particulate material in a fluid, in which such fluid is directed to flow through a passageway, at least a portion of the boundary of which is translucent to enable radiation to pass through that portion, viewing the flowing fluid through that portion by means of a camera which is constructed to generate electrical signals representative of the images it receives, and analysing those signals to provide data relating to the particulate material contained within the flowing fluid, using apparatus as set out in any one of the sixth to the immediately preceding paragraphs of the present specification.

The fluid analysed may comprise produced water from an oil well, and the image analysis may then be such as to distinguish between particulate material in the form of oil droplets and particulate material which is solid, such as particles of sand.

An example of apparatus for monitoring particulate material in a fluid in accordance with the present invention, as well as a method of monitoring particulate material in a fluid in accordance with the present invention, will now be described with reference to the accompanying drawings, in which:

FIG. 1 shows an axial sectional elevational view of the apparatus;

FIG. 2 shows an axial sectional view from above of the apparatus shown in FIG. 1;

FIG. 3 shows a cross-sectional elevational view of the apparatus shown in FIG. 1;

Figure 4:
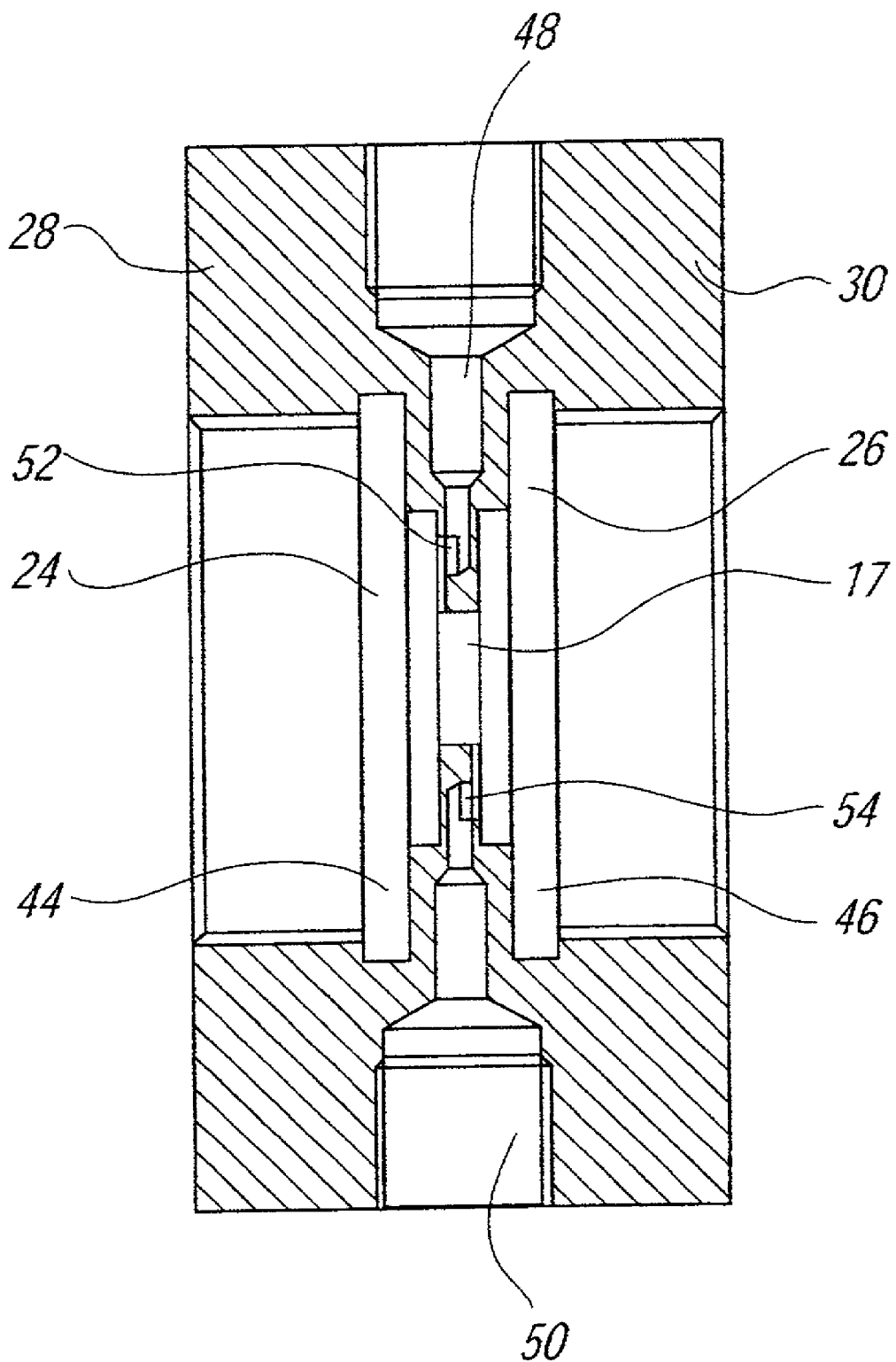
FIG. 4 shows, on a larger scale, parts of the apparatus shown in FIG. 1.

The apparatus shown in FIGS. 1 and 2 comprises a housing 10 which is substantially 450 mm long by 150 mm wide by 150 mm high and which has lower and upper parts 12 and 14. Extending in an intended vertical direction from above and from below the housing 10 are metal tubular portions 16 defining portions of a passageway 17 through which high pressure water produced from an oil well passes when the apparatus is in use (at pressures of about 30 Bar, possibly up to about 120 Bar, and temperatures of up to about 120° C.). In this apparatus, pipe connectors 18 and 20 are provided at the distal ends of the tubular portions 16.

The passageway 17 between the two tubular portions 16 extends through a high pressure cell 22 in the interior of the housing 10. At the centre of this cell 22, there are provided respective sapphire windows 24 and 26 on opposite sides of the passageway. These windows are held by respective clamp units 28 and 30 of the cell 22. Immediately adjacent to one of the sapphire windows 26 is a light emitting diode 32 held in place by an LED mounting bracket 34. A microscope unit 36 is arranged to view the interior of the passageway through the other sapphire window 24 so that the passageway interior is backlit by the diode 32. The microscope 36 comprises a lens 38 and a CCD video camera 40 mounted on a bracket 41 and spaced from the lens 38 by an aluminium alloy tube 42, the camera 40 being directed to view the interior of the passageway 17 via the lens 38.

FIG. 4 shows the sapphire windows 24 and 26 in greater detail. Thus, the sapphire windows 24 and 26 are held in place in their clamp units 28 and 30 by clamps 44 and 46, respectively. The windows 24 and 26 comprise sapphire plates which are parallel to one another but spaced apart, the space between them constituting part of the passageway 17. The internal sides of the sapphire windows 24 and 26 are provided with wash fluid inlets 48 and 50 which open on to the respective windows 24 and 26 via fanned jets 52 and 54, respectively. These can be connected to a reservoir of cleaning solution (not shown) or to a process line which carries the fluid to be monitored, and serve to dislodge any build-up of dirt on the windows 24 and 26.

Figure 5:
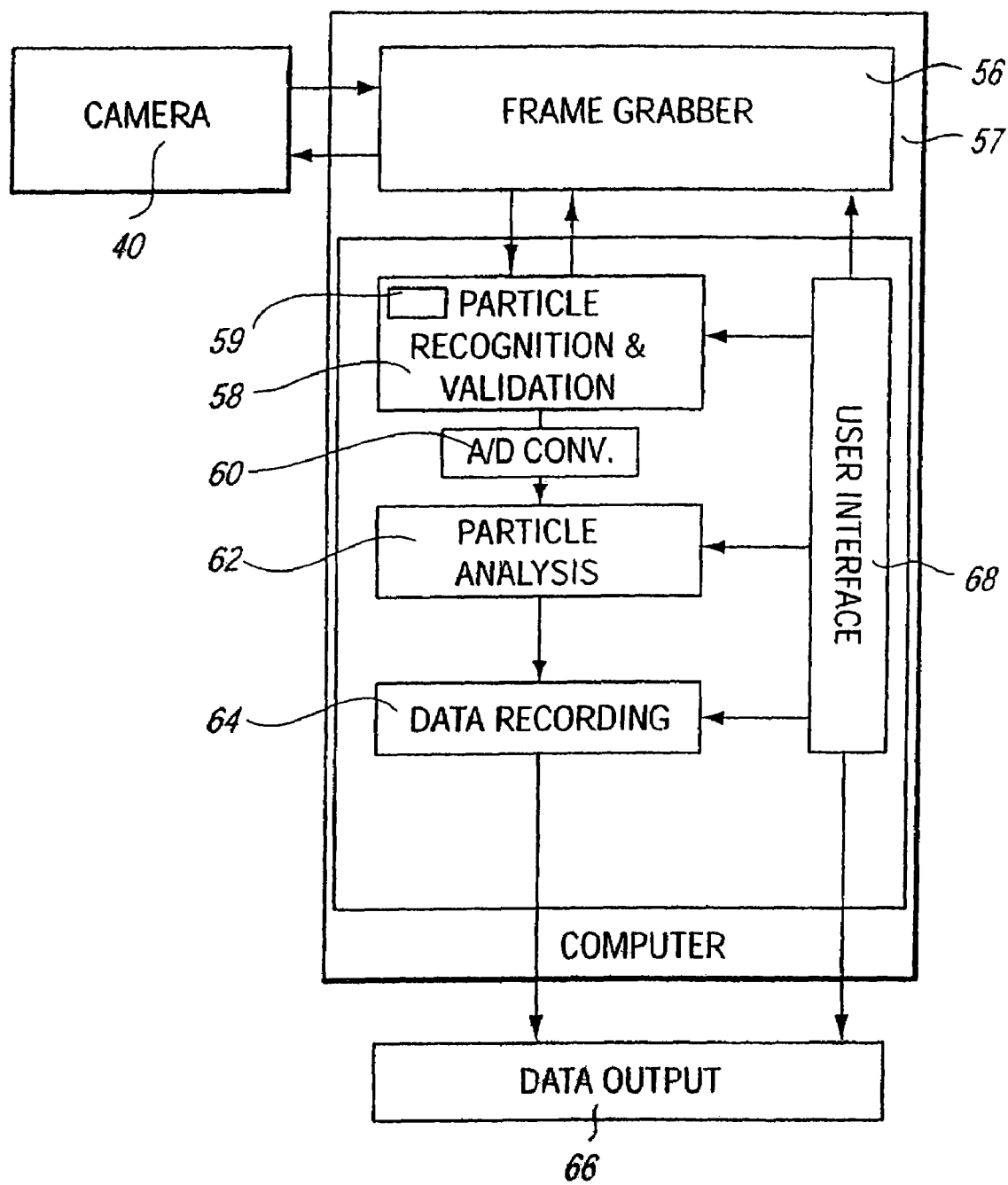
FIG. 5 shows a block circuit diagram of circuitry connected to a camera of the apparatus shown in FIG. 1.

The circuitry used in conjunction with the camera 40 is shown in FIG. 5. It comprises a frame grabber 56 provided as a frame grabber card located within a computer 57. The frame grabber 56 is connected to receive video signals from the camera 40 and to isolate successive frames from those signals. The circuitry further comprises particle recognition and validation means 58 (including a background memory 59) connected to receive signals from the frame grabber and to eliminate from the picture images of particles which are to be selectively excluded from the data, an analogue-to-digital converter 60 connected to receive signals from the recognition and validation means 58, a particle analyser 62 connected to receive signals from the converter 60 and a data recorder 64 connected to receive signals from the particle analyser 62. The recorded data can be viewed on a screen or a printer as a data output 66 of the circuitry and a user interface 68 is connected to the frame grabber 56, the particle recognition and validation means 58, the particle analyser recorder 62, the data recorder 64 and the data output 66 to enable a user to customise and make selections for each of the components of the circuitry.

It will be appreciated that the components of the circuitry other than the frame grabber 56 and the data output 66 are preferably parts of a duly programmed microprocessor.

Figure 6:
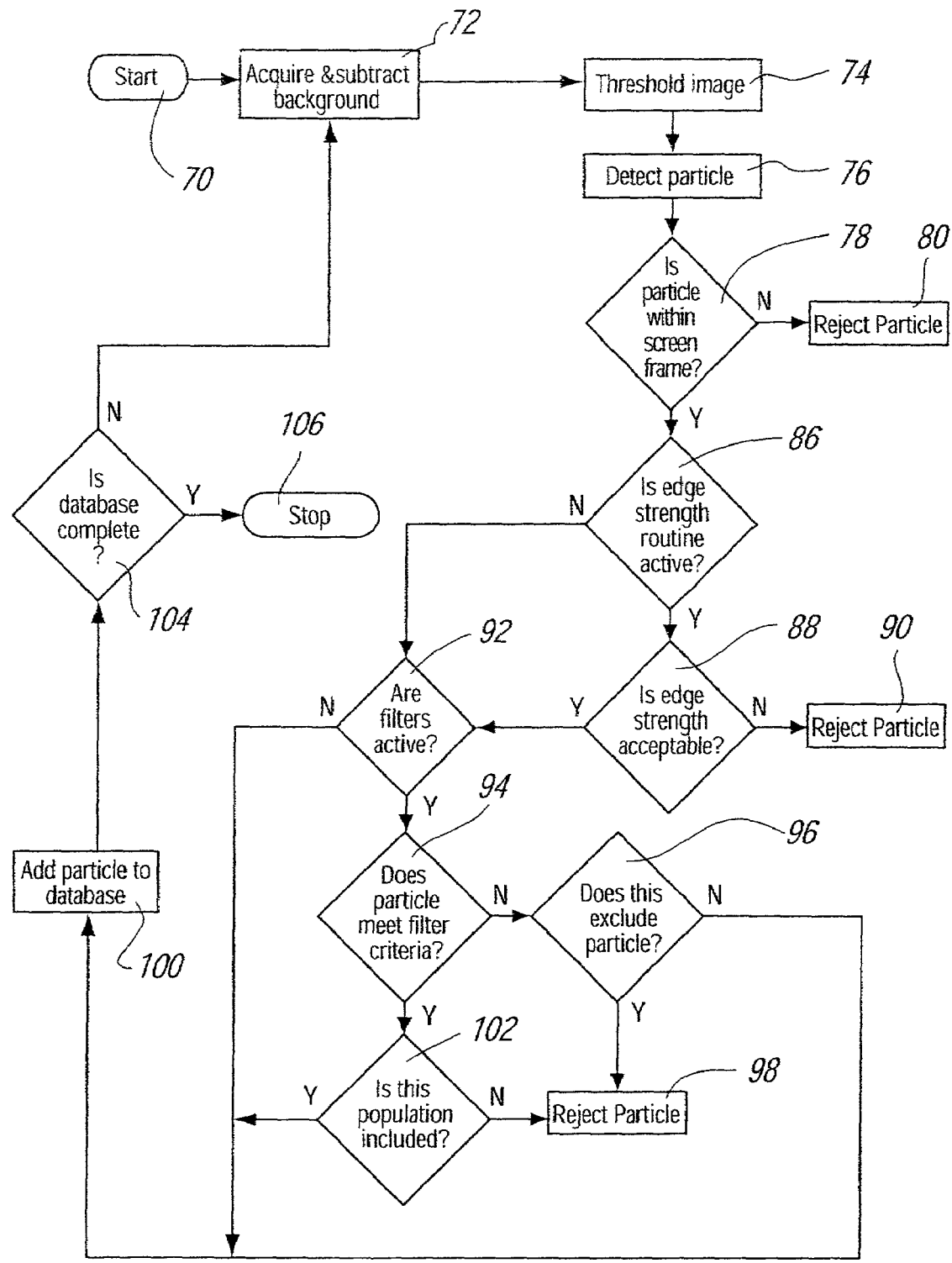
FIG. 6 shows a flow chart of successive steps executed by computer program loaded in the circuitry shown in FIG. 5.

The manner in which the apparatus operates will now be described in detail. In particular, the program executed by the particle recognition and validation means 58, the analogue-to-digital converter 60, the particle analyser 62 and the data recorder 64 is shown in FIG. 6. From the initiation 70 of this program, the background is stored in the background memory 59 and the background subtracted from a subsequent picture received from the frame grabber 56, at step 72 in FIG. 6. From this step, pixels having values equal to or below a given threshold value are rejected at step 74, being given the lower of the preset values, and those which are retained are given the higher of the two values. Particles within the field of view are identified at step 76. Its position within the field of view is identified and a check is made as to whether it is within the boundaries of the screen frame selected, at step 78. If the particle is outside the screen frame, it is rejected at step 80. If it is within the frame, a check is made whether the edge strength check has been activated by the user at step 86. If it is, a check is made as to whether the edge strength is acceptable at step 88, using analogue signals obtained at step 72. If it is not, then a check is made as to whether filters have been activated by the user, at step 92. If the edge strength routine has not been activated by the user at step 86, then the edge strength test is bypassed. If the filters have been activated by the user at step 92, then a check is made as to whether the filter criteria are met at step 94. This may involve counting the number of pixels lying on a given line across the particle image, or the number constituting the whole area of the particle image, or the number across the outside of the particle image to give its perimeter, and ascertaining whether the count lies above and/or below a preset threshold. Other filters may be made to ascertain whether one or more of the following parameters meet preselected criteria: centre of gravity, average feret diameter, aspect ratio (minimum to maximum feret diameter ratio), shape factor, specific length and/or width, estimated volume, area fraction (the area of the particle image as a fraction of the area of the field of view), Martin's Radii (radii from the centre of gravity), average Martin's Radius, fractal number (by comparing perimeters at successive decreasing sizes of pixel steps), concentration, curvature. If the filter criteria are not met at step 94, a further check is made as to whether this requires the particle to be excluded at step 96. If it does, the particle is rejected at step 98. If it does not, then the database is updated at step 100, by incrementing the relevant population count, as well as adding to the database all the measured parameters for that particle. This step 100 is also reached from the check on whether the particle meets the filter criteria at step 94 if the result was affirmative, and in addition whether the population meeting such criteria is to be included is checked at step 102. If that population is not to be included, then the particle is again rejected at step 98. Finally, a check is made at step 104 as to whether the database is complete. If it is not, then the routine beginning at step 72 is repeated; otherwise, the procedure is stopped at step 106.

Figure 7:
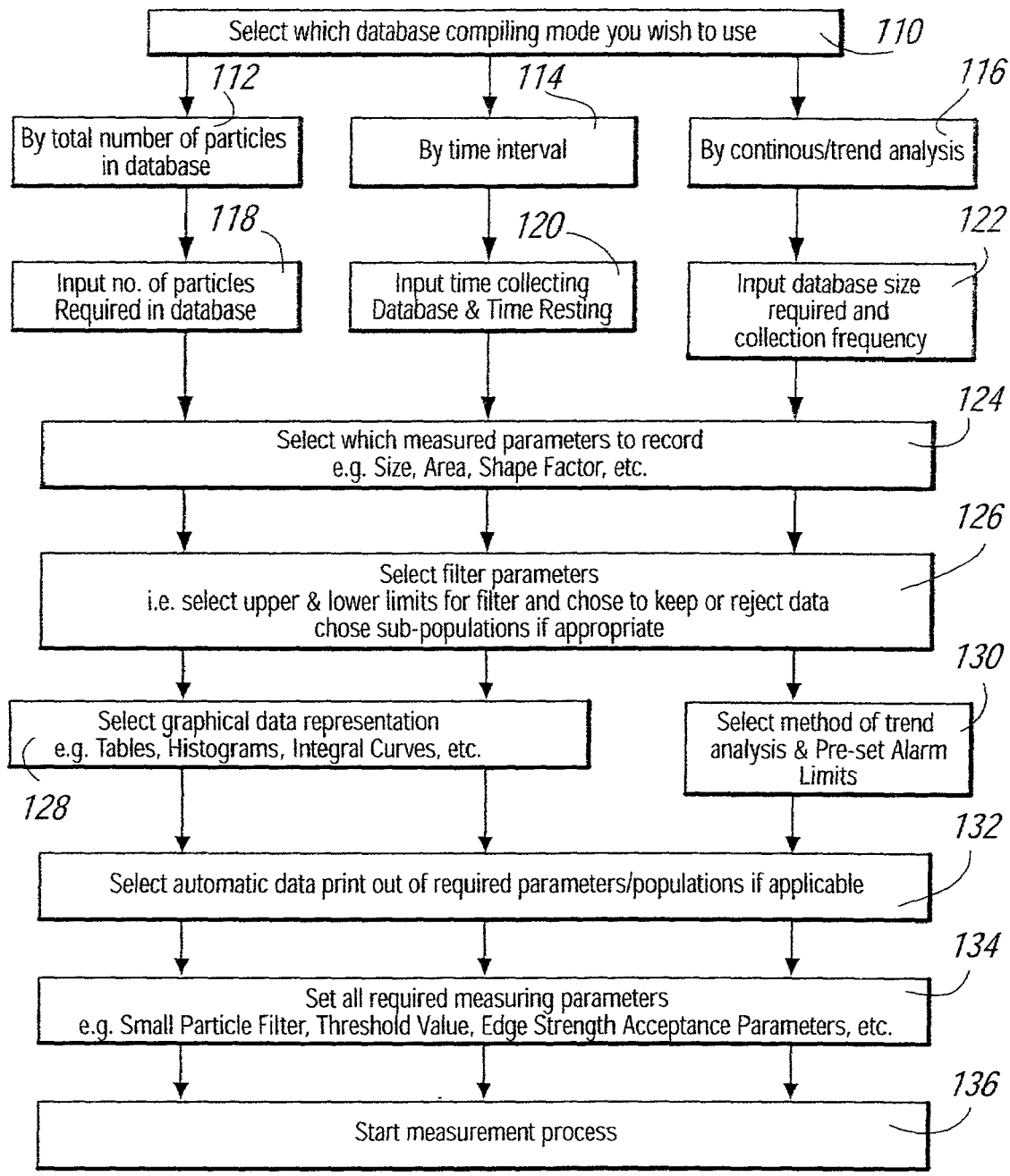
FIG. 7 shows possible options for the operation of the said foregoing computer program.

Selections which may be made by the user 88 are shown in FIG. 7. These selections are made by a proactive selection routine displayed on the computer screen with the aid of the keyboard and/or mouse. At step 110 in this routine, a selection is made as to which database compiling mode is desired. Whether it is by the total number of particles in the database (selection 112), by time interval (selection 114) or by continuous trend analysis (selection 116). These selections require further input from the user, being respectively the total number (for example 30,000) of particles required for the database (input 118), the time for collecting the database and the time for resting (input 120) (for example twenty minutes, or twenty minutes of each hour) and the database size required and collection frequency (for example once every 90 minutes) (input 122). Regardless of which selections were made initially, the parameters to be recorded, for example, size, area or shape factor are entered at step 124, and filter parameters, such as the upper and lower limits, the reduction criteria and the sub-populations desired are selected at step 126. For selections 112 and 114, a further selection is made regarding the manner in which the data is to be represented, whether by tables, histograms or integral curves at step 128. For an initial selection 116, a further selection of the method of trend analysis and pre-set alarm limits is made at step 130. Regardless of the initial selection which was made, an option may be made at step 132 to print out data automatically of the required parameters or populations if that is relevant. At step 134, all required measuring parameters, such as a small particle filter made at step 82 in FIG. 6, the threshold value for step 74, and the edge strength acceptance parameter for step 88, are entered, and lastly, the step for commencement of the monitoring process is initiated at step 136.

It will be appreciated that the function of the high pressure cell is to allow the camera 40 to see into the fluid to be monitored, that is also commonly referred to as the process stream, without changing the conditions within the process stream (such as its pressure and temperature).

The CCD camera 40 may be one which is similar to the type used in security surveillance systems. The lens 38 may be selectable from any one of a choice of magnifying objective lenses, so it is able to see very small particles within the process stream. For example, the set of lenses available may be as is common in microscopy, with magnifications of ×4, ×7 and ×10. As a result, the apparatus may be used to measure particles ranging in size from one micron ($1 \times 10^{-6}$ m) to a few millimeters.

With the illustrated apparatus, it is possible to carry out discrete sampling and perhaps use this data to monitor a particular batch of material or the effect of changing a particular process condition. By making periodic measurements it is possible to generate quality control information related to production periods. By trend (or continuous) measurement both the actual state of a process can be monitored and process upsets can be forecast, saving time and money.

The illustrated apparatus does not involve any assumption that it will be presented with a homogenous sample and it is possible to divide the particulates within a process stream in to sub-populations, that may have particular relevance to the production process. Up to eight sub-populations can be measured simultaneously, so that it would be possible, for example, to measure and monitor the concentration of both sand particles and oil droplets in the produced water of an oil well.

In regard to the last mentioned application, when oil is pumped out of the ground, it is a mixture of oil, water, solids and gases. It is relatively straightforward to remove the gases and the greater proportion of the oil from this mixture. What remains is mostly water with oil droplets and solids.

There are a number of different methods available to an oil producer to further extract enough of the oil from this mixture to make either re-injection or dumping viable. Some of these methods involve using chemicals to help the oil coalesce; these are expensive and hazardous. Some methods use mechanical separation techniques; these are subject to efficiency variations with, for example pump speeds, and can be damaged by high concentrations of solids. There are other techniques, nearly all of which benefit from monitoring oil droplet size, solids size and concentrations of both.

In most of these examples it is essential to monitor oil droplet size and concentration, for example, in order to use the absolute minimum quantity of chemicals, or to ensure hydrocyclones and centrifuges are operating at optimum speed. Often it is important to monitor the size and concentration of solids (sands) at the same time, to prevent blocking and/or abrasion, for example.

By using the filters within as described herein, the illustrated apparatus can simply differentiate between oil droplets and solids, within a single sample. Using the trend analysis routine also allows both monitoring of current conditions within the process and preventative measures to be taken if a process upset is predicted. Trend analysis also allows operators to monitor what effect a change in process conditions has.

Another possible use of the illustrated apparatus is in relation to high quality paper stocks (for example for bank notes). These may be made from cotton fibres, and may contain other materials such as fillers and pigments.

The length of the fibres used in the stock determine the strength and quality of the paper. The amount of filler and pigment affect the cost of production and paper colour. There is a further factor, fibrillation (how many side branches a fibre has and how long these are), that affects the paper. Fibres with a great degree of fibrillation become easily knotted and lumpy, whereas fibres with a small degree of fibrillation may not form a paper strong enough to use. Both the type of fibre used and the way the fibre is treated affect the degree of fibrillation.

By using appropriate filters within the illustrated apparatus, the latter can simply differentiate between fibres and fillers, or between liquid or solid particles within a single sample. Furthermore, by use of fractal analysis, the degree of fibrillation of the fibres can be determined.

For example, if a liquid stream is to be analysed that carries an emulsion and some solid particles, it would be possible to determine the size distribution for each of these populations individually. To effect this, a filter of shape factor is selected and whether a particle is liquid emulsion or solid can be determined by its shape factor. Liquid emulsions are spherical and have a shape factor approaching one, therefore a filter of shape factor 0.85 can be selected so that all particles which exceed 0.85 are recorded to the liquid database and particles below 0.85 are recorded to the solid database.

Users may filter the databases as above using the measured parameters. The software allows for the use of two filters combined. For example, if filter one AND filter two are passed, then the count is passed to population "x" in the database. If NEITHER filter one NOR filter two are passed, then the count is passed to population "y". If filter one but not filter two is passed, then the count is passed to population "z". Each outcome is stored to a database or discarded from the analysis according to user choice.

Regardless of the application for which the illustrated apparatus is being used, the trend analysis routine also allows both monitoring of current conditions within the process and preventative measures to be taken if a process upset is predicted. Trend analysis also allows operators to monitor what effect a change in process or stock conditions has. Thus, by gathering data for a particular function over a period of time, it is possible to predict if that function is going to increase or decrease over time. It is also possible to predict at what point the function might fall outside preset limits. For example, by monitoring particle size in a process for a period during satisfactory operation, it is possible to predict if that process may be tending to increased particle sizes and the point at which the particle size will be too large for satisfactory operation. A user message may be printed or displayed by the computer at this stage. Such a prediction can be made over the next two measuring periods at any given stage, and when there are only few points plotted, it can be made by a least squares line of best fit. When a larger number of data points are available, prediction could be by monitoring the rate of change of gradient of a linear regression.

More than one parameter may be monitored in this way at the same time, for one or more populations or sub-populations of particle meeting respective different criteria.

Any picture seen by the camera may of course be saved by means of the computer.

Thus, the illustrated apparatus provides a flexible instrument package, which can cater for any selected one of a large number of applications in a wide range of industrial processes.

A different light source may be used instead of the diode 52.

Control means may be provided to control the intensity of a light source.

A calibration factor is provided to enable pixel size to be converted to microns dependent on the magnification of the lens in use.

Visual prompt type warnings are given if the user attempts to discard measured data without saving it.

Visual prompt type warnings are also given if the user attempts to set filters or database parameters that are impossible, for example if a particle is required to have an aspect ratio >0.7 and at the same time an aspect ratio <0.7, or if a command is given to collect data for the first twenty minutes of each fifteen period.

The illustrated apparatus can make available results in relation to an individual particle, an individual image, a database of particles, and trend statistics.

What is claimed is:

1. An apparatus for monitoring particulate material in a flowing fluid comprising:
    a passageway, through which fluid to be monitored is passed, at least a portion of the passageway being translucent to enable radiation to pass through that portion;
    a camera, which is arranged to receive such radiation and which is constructed to generate electrical signals having a multiplicity of different values respectively representative of different values of a grey scale, the signals being representative of the images received by the camera;
    a frame grabber connected to the camera to isolate a frame from the signals generated by the camera;
    a background memory connected to the frame grabber to store data indicative of the value of background signals of the images seen by the camera;
    subtraction means connected to the background memory and to the frame grabber to subtract the stored values of the background signals from the values of the signals of a subsequent frame isolated by the frame grabber;
    an image analyzer configured to receive signals of successive frames from the frame grabber after said subtraction of values by said subtraction means, so as to provide data on successive isolated frames relating to particulate material within the flowing fluid; and
    out-of-focus elimination means, said out-of-focus elimination means being configured to eliminate a particle image which is out of focus by checking the rate of change in the value of signals received for successive pixels from a position away from the particle to a position within a boundary of the particle image and eliminating that particle image if the rate of change of the values of the signals does not exceed a threshold value.

2. An apparatus according to claim 1, in which said portion of the passageway is transparent.

3. An apparatus according to claim 1, in which the camera is a still camera triggered to operate by the image analyzer.

4. An apparatus according to claim 1, in which the camera is a Charged Coupled Device (CCD) camera.

5. An apparatus according to claim 1, in which the radiation is in the visible range of the electromagnetic spectrum.

6. An apparatus according to claim 1, in which said electrical signals representing a grey scale range in value from zero to 255, wherein a zero value relates to a darkest image and a 255 value relates to a brightest image, or vice versa.

7. An apparatus according to claim 1, in which the apparatus further comprises an analog-to-digital converter in which a pixel having a value beyond a threshold value in the analog input is accorded one of two values in the digital output, and a pixel having a value equal to or below the threshold value is accorded the other of the two values in the digital output.

8. An apparatus according to claim 1, further comprising edge-of-field elimination means to eliminate any particle image which is closer than a predetermined distance to the edge of the field of view.

9. An apparatus according to claim 1, in which the fluid is backlit so that silhouettes of the particles are viewed.

10. An apparatus according to claim 1, in the said portion comprises at least one sapphire window, said window being substantially resistant to scratching so as to remain transparent.

11. A method of monitoring particulate material in a fluid, comprising:
    directing a fluid to flow through a passageway having a boundary, at least a portion of the boundary of said passageway being translucent to enable radiation to pass through that portion;
    viewing the flowing fluid through that portion by means of a camera which is configured to generate electrical signals representative of the images it receives; and
    analyzing said electrical signals to provide data relating to the particulate material within the flowing fluid, using the apparatus as claimed in claim 1.

12. A method according to claim 11, in which the fluid comprises water from an oil well.

13. A method according to claim 12, in which the the analyzing distinguishes between particulate material in the form of oil droplets and particulate material which is solid.

14. An apparatus for monitoring particulate material in a flowing fluid comprising:
    a passageway, said passageway being configured to pass fluid for monitoring and being at least partially translucent;

a camera, said camera being arranged to receive radiation through said translucent portion of said passageway and being configured to generate electrical signals representative of grey scale values of images received by the camera;

a frame grabber, said frame grabber being configured to isolate a frame from the signals generated by the camera;

a background memory, said background memory being configured to store data relating to background signals of the images received by the camera;

subtraction means, said subtraction means being configured to subtract values of the background signals from values of the signals of said frame;

an image analyzer, said image analyzer being configured to provide data relating to the particulate material within the flowing fluid based on data from said frame grabber and said subtraction means; and edge-of-field elimination means to eliminate any particle image which is closer than a predetermined distance to the edge of the field of view.

15. An apparatus for monitoring particulate material in a flowing fluid comprising:

a passageway, said passageway comprising a sapphire window and being configured to pass fluid for monitoring past said window;

a camera, said camera being arranged to receive radiation through said sapphire window of said passageway and being configured to generate electrical signals representative of grey scale values of images received by the camera;

a frame grabber, said frame grabber being configured to isolate a frame from the signals generated by the camera;

a background memory, said background memory being configured to store data relating to background signals of the images received by the camera;

subtraction means, said subtraction means being configured to subtract values of the background signals from values of the signals of said frame; and an image analyzer, said image analyzer being configured to provide data relating to the particulate material within the flowing fluid based on data from said frame grabber and said subtraction means.

* * * * *